US006316458B1

(12) United States Patent
Nadler et al.

(10) Patent No.: US 6,316,458 B1
(45) Date of Patent: Nov. 13, 2001

(54) METHOD OF ENHANCING INSULIN ACTION

(75) Inventors: Jerry L. Nadler, Charlottesville, VA (US); Thomas W. Balon, Covina; Yoko Yamaguchi, Glendora, both of CA (US)

(73) Assignee: Cell Therapeutics, Inc., Seattle, WA (US)

( * ) Notice: Subject to any disclaimer, the term of this patent is extended or adjusted under 35 U.S.C. 154(b) by 0 days.

(21) Appl. No.: 09/557,318

(22) Filed: Apr. 25, 2000

Related U.S. Application Data

(60) Provisional application No. 60/132,003, filed on Apr. 30, 1999.

(51) Int. Cl.[7] .................................................. A01N 43/90
(52) U.S. Cl. ........................ 514/263; 514/258; 514/262; 514/263
(58) Field of Search ............................................. 514/263

(56) References Cited

U.S. PATENT DOCUMENTS 5,648,357   7/1997   Bianco et al. .

OTHER PUBLICATIONS

"Diabetes in America", National Diabetes Data Group, 2nd Edition, 1995, pps. iii–v.

D. LeRoith et al., "Diabetes Mellitus", Lippincott–Raven, 1996, pps. 509–519.

J. Després et al., "Hyperinsulinemia An An Independent Risk Factor For Ischemic Heart Disease", New England Journal of Medicine, 1996, pps. 952–957.

A. Dunaif et al., "The Insulin–Sensitizing Agent Troglitazone Improves Metabolic and Reproductive Abnormalities in the Polycystic Ovary Syndrome", Journal of Clinical Endocrinology and MEtabolism, 1996, vol. 81, No. 9, pps. 3299–3306.

S. Haffner et al., "Insulin Resistance Implications for Type II Diabetes Mellitus and Coronary Herat Disease", The American Journal of Medicine, 1997, vol. 103, No. 2, pps. 152–162.

G. Howard et al., "Insulin Sensitivity and Atherosclerosis", Circulation, vol. 93, No. 10, 1996, pps. 1809–1817.

E. Ferrannini, M.D. et al., "Insulin Resistance In Essential Hypertension", The New England Journal of Medicine, 1987, vol. 317, No. 6, pps. 350–357.

C. Tack, M.D. et al., "Troglitazone Decreases the Proportion of Small, Dense LDL and Increases the Resistance of LDL to Oxidation in Obese Subjects", Diabetes Care, vol. 21, No. 5, 1998, pps. 796–799.

B. Sobel, M.D., "Potentiation of Vasculopathy by Insulin", Circulation, vol. 93, No. 9, 1996, pps. 1613–1615.

A. Gennaro, "Solutions, Emulsions, Suspensions, and Extracts", Remington's Pharmaceutical Sciences, Chapters 83092, 1990, pps. 1519–1714.

T. Balon et al., "Magnesium supplementation reduces development of diabetes in a rat model of spontaneous NIDDM", American Journal of Physiological, vol. 269, No. 4, 1995, pps. E745–E752.

T. Balon et al., "Nitric oxide release is present from incubated skeletal muscle preparations", Journal of Applied Physiology, vol. 77, No. 6, 1994, pps. 2519–2521.

T. Balon et al., "Dietary Magnesium Prevents Fructose–Induced Insulin Insensitivity in Rats", Hypertension, vol. 23, No. 6, 1994, pps. 1036–1039.

"Drug Information for the Health Care Professional", vol. 1, 17th Edition, pps. 1662–1675.

*Primary Examiner*—James H. Reamer
(74) *Attorney, Agent, or Firm*—Foley & Lardner

(57) ABSTRACT

A category of hydroxyalkyl-substituted xanthines are useful in treating patients suffering from disorders associated with impaired glucose metabolism or impaired insulin function. Use of these compounds, for example, restores insulin responsiveness in otherwise insulin-resistant Type 2 diabetic patients, thus reducing elevated blood glucose levels. The subject compounds also act to restore certain defects of lipid metabolism and to enhance the effects of insulin in general. Insulin-enhancing compositions and methods of treating disorders of glucose metabolism are provided.

12 Claims, 2 Drawing Sheets

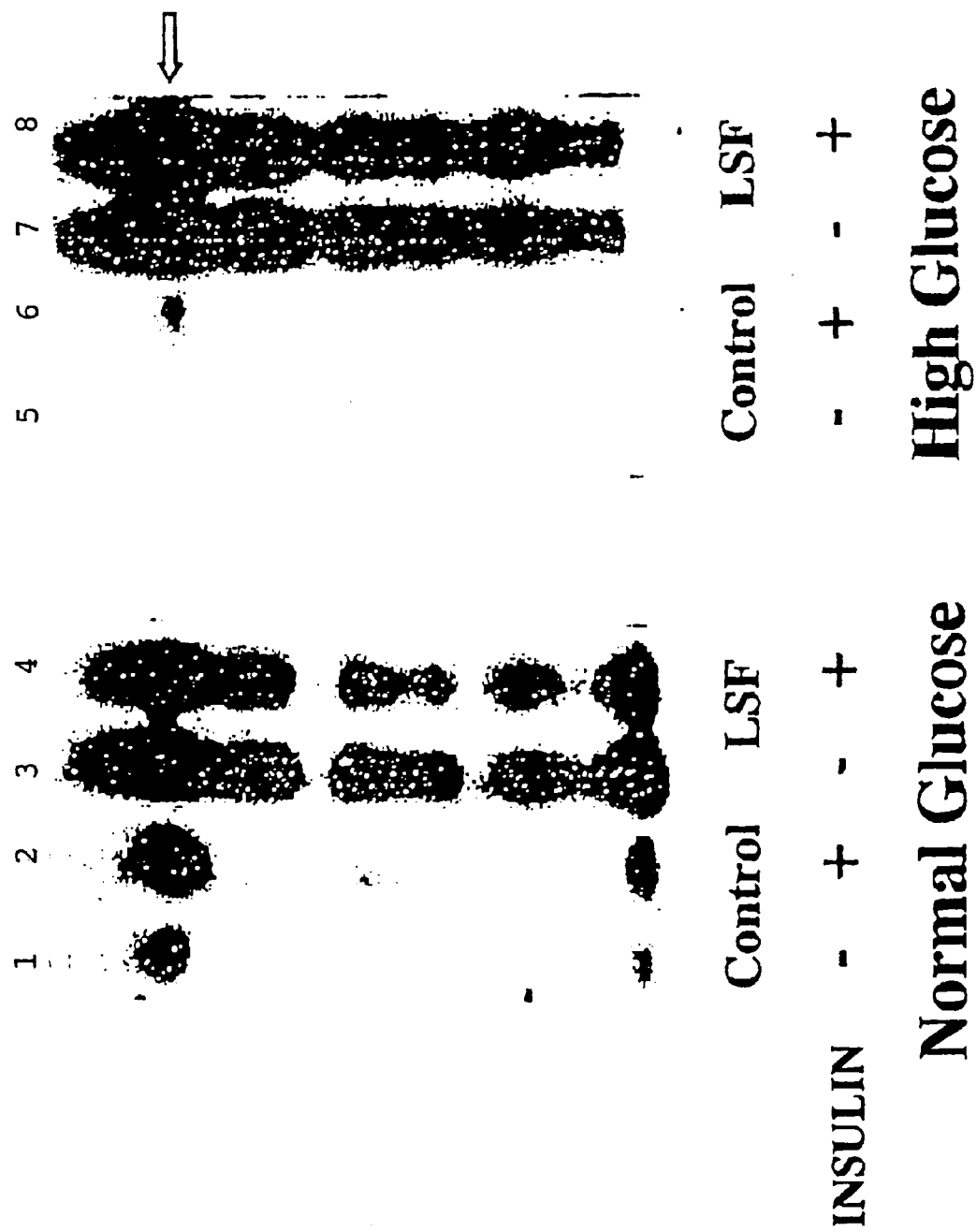

METHOD OF ENHANCING INSULIN ACTION

This application is based on Provisional application Ser. No. 60/132,003 filed Apr. 30, 1999.

BACKGROUND OF THE INVENTION

Insulin resistance is defined as a state associated with low or impaired biologic response to insulin. Insulin resistance may include altered sensitivity to any biologic action of insulin, including effects on carbohydrate, lipid or protein metabolism. Further, insulin action in enhancing nitric oxide release and vascular smooth muscle relaxation may be impaired in an insulin resistant patient.

The best studied disease associated with insulin resistance is Type 2 diabetes. Type 2 diabetes, previously called adult-onset diabetes or non-insulin dependent diabetes mellitus type (NIDDM), results principally from one of two defects. One is that β islet cells are defective in secreting sufficient insulin in response to an elevation in blood glucose. The other is that target cells, such as adipocytes and skeletal muscle cells, do not respond to an increase in insulin by elevating glucose transport. Interestingly, the insulin receptors and at least some parts of the insulin signaling pathways in these patients suffering Type 2 diabetes appear to be normal. Patients with diabetes suffer from the effects of prolonged elevation of blood glucose levels.

There have been extensive studies to identify the biochemical and genetic factors leading to Type 2 diabetes and impaired glucose tolerance. National Diabetes Data Group, *Diabetes In America* 2nd Ed. NIH publication No. 95-1468, 1995. Most investigators believe that the initial biochemical defect is the reduction of insulin mediated glucose uptake, which worsens with age and adiposity. However, Type 2 diabetes develops only upon some reduction in insulin secretion. This defect is in the β cells, and it is specific for the reduction of the glucose-induced insulin secretion. Such a defect may occur at any age, but usually after the age of 35 years. Moreover, glucose itself can lead to a further impairment of insulin action.

The prevalence of diabetes is rapidly increasing. Nearly 6% of the general population has diabetes of which 95% have Type 2 diabetes. The rate is even higher in minorities and in people over the age of 65 (10.5%). Data in 1992 showed that $1 in every $7 spent in health care in this country was spent on the care for people with diabetes. New treatments to control the above-detailed parameters will improve the health care of people with diabetes, and any treatment that reduces the rate of diabetes development or mitigates the rate at which diabetic patients develop complications will advance the treatment options available to the diabetic. Current treatments, however, are insufficient.

Insulin resistance is also associated with conditions other than Type 2 diabetes, however. Reduced insulin action is also associated with other factors, including certain drugs, like corticosteroids, growth hormone, thiazide diuretics, stress hormones, increased fat intake, and cytokines, such as tumor necrosis factor. Insulin resistance is also common in all of the people with simple obesity and impaired glucose tolerance (IGT), as well as a substantial percentage of the people with essential hypertension and atherosclerosis. A syndrome associating insulin resistance with increased cardiovascular disease has also been described.

"Syndrome X" is a clustering of abnormalities, including dyslipidemia, hypertension, coronary artery disease, central obesity, hyperuricemia, impaired fibrinolysis, polycystic ovary syndrome (PCOS) in women, glucose tolerance and insulin resistance. Reaven, DIABETES MELLITUS, pp. 509–19, Le Roth et al, eds. (1996). Moreover, fasting hyperinsulinemia (a marker of insulin resistance) is associated with cardiovascular disease and, like high triglyceride levels, hyperinsulinemia is an independent risk factor in comoary artery disease, even in non-diabetic subjects. Despres et. al. New Engl. J. Med. 334: 952–57 (1996). Studies suggest that decreasing insulin resistance is helpful treating the above-mentioned conditions, including PCOS (Dunaif et al., J. Clin. Enocrinol. Metab. 81: 3299–3306 (1996) and IGT (Antonucci et al., 83: 1818–20 (1998)).

Insulin resistance is also associated with low high density lipoprotein cholesterol and a shift toward smaller, denser, low density lipoprotein cholesterol particles, which are more atherogenic. Insulin resistance is also associated with hypertension, particularly in whites. The link of insulin resistance to cardiovascular disease is further substantiated by epidemiology (Haffner et al., Am. J. Med. 103: 152–62 (1997); Howard et al., Circulation 93: 1809–17 (1996)), by studies evaluating its role in blood pressure regulation (Ferranni et al., New Engl. J. Med. 317: 350–57 (1987)), and by the observation that drugs that improved insulin action can decrease the proportion of small dense low density lipoprotein particles in obese subjects (Tack et al., Diabetes Care 21: 796–99 (1998). Other studies show that insulin can potentiate vascular disease by reducing fibrinolysis (Sobel, Circulation 93: 1613–15 (1996).

In view of the foregoing, it is apparent that a need exists in the art of for new and improved compositions and therapeutics methods that ameliorate insulin resistance and are thus useful in treating the foregoing conditions.

SUMMARY OF THE INVENTION

It is, therefore, an object of the invention to provide methods of improving insulin action in a patient. According to this object, the invention provides a method that increases the action of insulin, which helps control glucose metabolism. In general, this method entails administering an effective amount of a xanthine-based compound, or its pharmaceutically acceptable salt, having the following structure:

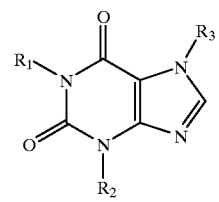

wherein: $R_1$ is an R enantiomer of an ω-1 secondary alcohol-substituted alkyl ($C_{5-18}$), wherein said alcohol moiety can be esterified; $R_2$ is alkyl ($C_{1-12}$), which may have one or two nonadjacent oxygen atoms in place of a carbon atom; and $R_3$ is $CH_3$ or H. A preferred method utilizes lisofylline. This method is useful, for example, in treating obesity, cardiovascular disease, hypertension, dyslipidemia, coronary artery disease, hyperuricemia, impaired fibrinolysis, polycystic ovary syndrome, impaired glucose tolerance and Type 2 diabetes.

It is another object of the invention to provide methods of treating lipid disorders that are associated with Type 2 diabetes. According to this object of the invention, a method of treating Type 2 diabetes-associated lipid disorders is provided. This method entails administering an effective amount of a xanthine-based compound or its salt, described above.

It is still another object of the invention to provide methods useful in treating disorders associated with impaired glucose uptake. According to this object of the invention, a method is provided that increases tissue glucose uptake. This method typically involves contacting the impaired tissue with an effective amount a xanthine-based compound or its salt, as described above.

It is yet an additional object to provide methods useful in treating disorders associated with abnormal triglyceride production. Further to this object, a method is provided that inhibits triglyceride formation. In general, this method prescribes administering an effective amount a xanthine-based compound or its salt, as described above.

Still a further object of the invention is to provide compositions having enhanced insulin activity. According to this object, an insulin-enhancing composition is provided. This composition contains insulin, or an insulin-like compound, in combination with a xanthine-based compound or its salt, as described above.

BRIEF DESCRIPTION OF THE DRAWINGS

FIG. 2. shows that lisofylline treatment restores insulin-promoted insulin receptor phosphorylation in a model for insulin tolerance.

DETAILED DESCRIPTION OF THE INVENTION

Figure 1:
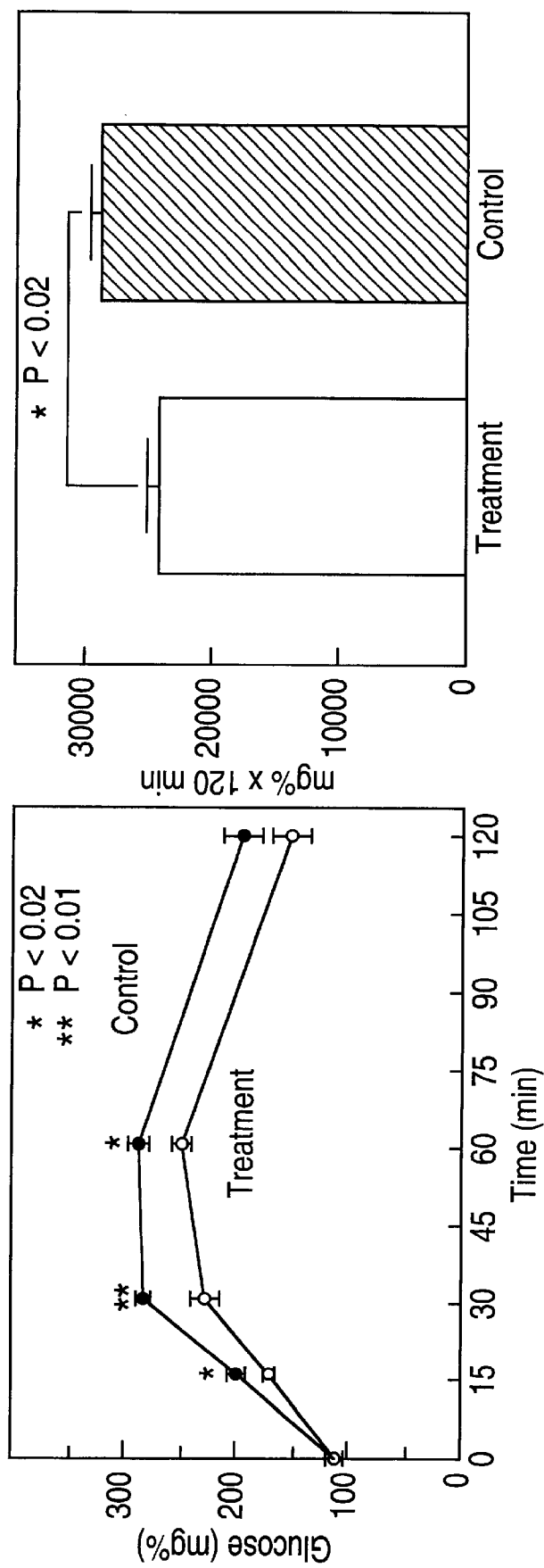
FIG. 1. shows oral glucose tolerance in ZDF rats untreated or treated with lisofylline. The left panel show the curve and the right panel shows the integration of that curve.

It has been found that diabetic patients suffer, at least in part, due to an interruption in the signaling pathway through insulin receptors. As a result, high blood glucose levels accumulate which has many documented adverse effects, including the formation of glycation products. The present invention, responding to a need for medicaments able to correct the defects and reverse the symptoms of the diabetic patient, provide herein a group of xanthine-based compounds. Treatment with the below-described compounds can restore normal kinase activity of the insulin receptor signaling pathway or increase glucose uptake in fat or skeletal muscle cells.

Without being bound to a particular theory, it is hypothesized that xanthine-based compounds, described in more detail below, are useful to alleviate the symptoms of Type 2 diabetes in at least two different ways. First, data shown below suggests that the present compounds can be used to lower blood glucose level, acting to by-pass the insulin receptor. In effect, they may act as a pseudoinsulin, stimulating the uptake of glucose by intervention in the insulin signaling pathway. In this way, they can be used either alone or in conjunction with insulin to reduce blood glucose levels. Second, it is also possible that the present compounds actually directly restore insulin fuiction in this insulin non-responsive disorder.

The methods of the invention are useful in improving glucose tolerance in people with impaired glucose tolerance (IGT). Eleven percent of the U.S. population has IGT, and this disorder is associated with increased incidence of ischemic heart disease, a new therapeutic method would have a clear and wide spread indication. Since the present methods appear to act, at least in part, by circumventing insulin in activating the same pathway to stimulate glucose uptake, they may be used for pharmaceutical intervention in this area.

The present methods of increasing insulin action are also applicable to reversing or attenuating the insulin impairment associated with factors like certain drugs, including corticosteroids, growth hormone, thiazide diuretics, stress hormones, increased fat intake, and cytokines, such as tumor necrosis factor. They are also useful in attenuating insulin resistance in people with simple obesity, essential hypertension and atherosclerosis, as well as in treating cardiovascular disease and hypertension. "Syndrome X," and the associated abnormalities, like dyslipidemia, hypertension, coronary artery disease, central obesity, hyperuricemia, impaired fibrinolysis, polycystic ovary syndrome (PCOS) in women, glucose tolerance and insulin resistance, are also therapeutic targets.

Thus, the present invention is drawn to enhancing and/or restoring the effects of insulin. In the case of the Type 2 diabetes patient and the patient afflicted with IGT, for example, the inventive methods act both to enhance the effects of insulin and to overcome insulin resistance.

Compounds Useful in the Invention

Compounds generally usefull in the invention are based on a xanthine core, which is typically substituted at the 1, 3 and/or 7 positions. Pharmaceutically acceptable salts of these compounds are envisioned as equally useful. These compounds are referred to herein as "xanthine-based compounds." The prototypical xanthine-based compound is lisofylline (LSF), and in general, unless otherwise indicated, when lisofylline is referred to herein as useful, that reference may be understood generally to apply to other members of the class of xanthine-based compounds described herein. Particularly useful xanthine-based compounds are disclosed in U.S. Pat. No. 5,648,357, which is hereby incorporated by reference its entirety. Methods of preparing these compounds may be found therein, as well. More specifically, the preferred compounds useful in the invention have the following structure:

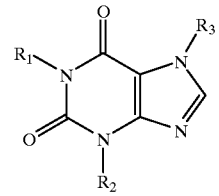

wherein $R_1$ is an R enantiomer of an ω-1 secondary alcohol-substituted alkyl $(C_{5-8})$, wherein $R_2$ is alkyl $(C_{1-12})$, optionally containing one or two nonadjacent oxygen atoms in place of a carbon atom, and $R_3$ is $CH_3$ or H. Among this group of compounds with a xanthine core structure, the particularly preferred compound is lisofylline, 1-(5-R-hydroxyhexyl)-3,7-dimethylxanthine.

It will be recognized that the alcohol-substituted alkyl portions of the foregoing molecules may be esterified, to yield further xanthine-based compounds that are active per se or as prodrugs. Small $C_{1-6}$ carboxylic acid esters are preferred and may be made according to standard synthetic techniques. It is anticipated that such compounds will have improved phanmacodynamic properties, such as improved circulating half-life. In addition, any pharmaceutically acceptable salt of the foregoing (esterified or non-esterified) compounds may also substitute in the methods of this invention.

Pharmaceutical Formulations

The pharmaceutical compositions employed in the methods of the invention generally contain a therapeutically effective amount of at least one xanthine-based compound, as described above. Preferably, this compound is mixed with a pharmaceutically acceptable carier.

Due to the complementary action of the foregoing xanthine-based compounds with the action of insulin, it is advantageous to use and to formulate the two medicaments together. For some patients, administration of these combined formulations reduce the amount of insulin given to the patient. Co-formulations with molecules that stimulate insulin secretion are also envisioned. Such molecules include the sulfonylureas.

Thus, the present invention also specifically contemplates therapeutic compositions for treating a diabetic patient, which comprise any compound having insulin-like activity, including insulin, insulin derivatives and analogs of insulin, in combination with one or more xanthine-based compounds. Therapeutic formulations of insulin and insulin-like molecules are well known in the medical arts and it will be understood that the present compositions may be essentially based on any medically useful insulin formulation, except that the inventive compositions incorporate an effect amount of one or more xanthine-based compounds. Examples of formulations containing insulin or insulin derivatives may be found in DRUG INFORMATION FOR THE HEALTH CARE PROFESSIONAL, 17th ed., vol. 1, pp. 1662–75 (1997), which is hereby incorporated by reference.

The skilled artisan will recognize, that "insulin-like" compounds are those that mimic one or more of the biological activities of insulin. The biological activity of insulin is well-established, and includes the mediation of tissue uptake of glucose. Thus, one class of insulin-like compounds that have insulin-like activity are insulin derivatives. These derivatives generally are based on the insulin protein itself, and retain insulin activity. They are protein-based and have substantial amino acid identity with human, porcine or other forms of insulin currently used medicinally. Many such derivatives are known and under study.

On the other hand, insulin-like compounds (like the xanthine-based molecule described herein) may mimic insulin activity by directly triggering pathways responsible for glucose uptake, thus circumventing the insulin receptor. Defects in the insulin receptor have been implicated in reduced insulin action, especially in Type 2 diabetes. One such class of drugs are thiazolidinediones, which include troglitazone (Rezulin®, Parke-Davis), ciglitazone, rosiglitazone and pioglitazone. Thus, like the thiazolidinediones, xanthine-based compounds are particularly suited to treat Type 2 diabetes and certain other disorders associated with glucose intolerance and/or decreased insulin fiction. The present molecules, however, work in the absence of insulin (as shown by the data below), in contrast to the thiazolidinediones, which work only in the presence of insulin.

An effective amount of a xanthine-based compound in the context of insulin compositions is an amount sufficient to enhance the action of insulin by at least about 10% (e.g., decrease blood glucose levels). More preferred compositions contain an amount of xanthine-based compound sufficient to enhance the action of insulin by at least about 20% and most preferred compositions would contain an amount of xanthine-based compound sufficient to enhance insulin action by at least about 30%.

A suitable formulation will depend on the nature of the disorder to be treated, the nature of the medicament chosen, and the judgment of the attending physician In general, the xanthine-based compounds are formulated either for oral administration or injection, although other modes of administration such as transmucosal or transdermal routes may be employed. Suitable formulations for these compounds, including pharmaceutically acceptable excipients, can be found, for example, in REMINGTON'S PHARMACEUTICAL SCIENCES, chapters 83–92, pages 1519–1714 (Mack Publishing Company 1990) (Remington's), which is hereby incorporated by reference.

If a solid carrier is used, the preparation of xanthine-based compound can be tableted. The composition can be placed in a hard gelatin capsule in powder or pellet form or in the form of a troche or lozenge. The amount of solid carrier will vary widely but preferably will be from about 25 mg to about 1 gram.

Where the composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions or suspensions may be considered, for example, aqueous gums, cellulose, silicates or oils and are incorporated in a soft gelatin capsule shell.

When a liquid carrier is used, the preparation may be in the form of a syrup, emulsion, soft gelatin capsule, sterile injectable liquid such as an ampule or non-aqueous liquid suspension.

A syrup formulation will generally consist of a suspension or solution of the compound or salt thereof in a liquid carrier with a flavor or coloring agent. Examples of liquid carriers include ethanol, polyethylene glycol, coconut oil, glycerin and water.

Although other routes of administration are contemplated, the pharmaceutical compositions of the invention preferably are suitable for oral and parenteral administration. Parenteral administration can include intravenous ("i.v."), intramuscular ("i.m."), subcutaneous ("s.c."), intranasal, intrarectal, intravaginal, intraperitoneal ("i.p.") ex vivo culture, or topical delivery. Preferred administration is accomplished intravenously, especially when administered with insulin.

Appropriate dosage forms for each specific route of administration may be prepared by conventional techniques. A typical dosage form for parenteral administration is a solution or suspension of at least one xanthine-based cornpound, or its pharmaceutically acceptable salt. The parenteral dosage form typically contains a parenterally acceptable sterile aqueous or non-aqueous carrier. The parenteral dosage form optionally contains a parenterally acceptable oil or polymer. Examples of such oils and polymers include polyethylene glycol, polyvinylpyrrolidone, lecithin, arachis oil, and sesame oil. Parenteral acceptability is known to the skilled clinician.

Formulation as a standard unit dose is also contemplated. Thus, the pharmaceutical compositions of the invention can be formulated, for example, for oral use in dosage unit form as a pill, a tablet, a caplet, or a capsule. These dosage units may each contain a therapeutically effective amount of one or more xanthine-based compounds. These dosage units also may contain sub-therapeutically effective amounts, where multiple units may be combined to achieve a therapeutically effective amount.

The amount of xanthine-based compound in a unit dose will depend on many factors considered by the skilled clinician. Generally, however, dosage units prepared for use will contain from about 500 mg to about 1500 mg of at least one xanthine-based compound. A typical parenteral dose can be from about 500 mg to about 5 g and may be administered (i.v., i.p., i.m., or s.c.) over a course of 24 hours. A typical topical formulation contains from about 1% to about 4% by weight. An ex vivo culture concentration, for use in the transplantation methods described below, can be maintained from about 10 μM to about 500 μM.

Finally, xanthine-based compounds may be formulated with an effective amount of insulin or an insulin-like compound. The normal dosage for administration of insulin has been well described. DRUG INFORMATION FOR THE HEALTH CARE PROFESSIONAL, supra, p. 1667. Conventional therapy consists of 1 or 2 insulin injections a day. Intensive therapy provides 3 or more insulin injections a day or may utilize an insulin pump. The dosage and timing of administering insulin must be determined for each patient by the attending physician. After receiving insulin after first diagnosis, some patients continue insulin treatment in small doses of 0.2 to 0.5 USP units per kg of body weight. Where at least one xanthine-based compound is included, less insulin generally will be required, but the exact amounts will be determined by the attending physician.

Methods of the Invention

The methods of the present invention generally comprise administering a therapeutically effective amount of at least one xanthine-based compound, described herein, to a patient suffering from a disorder involving diminished insulin action or a defect in glucose metabolism, like those described above. These methods modulate the insulin receptor signaling pathway, enhancing the effects of insulin or bypassing insulin altogether. Some preferred methods lower elevated blood glucose and/or triglyceride levels in a patient. The patient may be a human or a non-human animal. It will be recognized that the optimal timing for administering the xanthine-based compounds will be determined by the clinician.

The need for this treatment ultimately will be based on the evaluation by a skilled clinician in the diabetes art. Generally, however, a patient will be in need of such treatment to lower the blood glucose level and/or inhibit triglyceride formation.

In particular, the invention contemplates a method of treating a patient suffering from Type 2 diabetes, comprising administering to the patient an effective amount of lisofylline and/or at least one derivative thereof.

An additional method within the scope of the present invention involves treating Type 2 diabetes-associated lipid abnormalities. This results from the ability of xanthine-based compounds to inhibit the formation of, or reduce the levels of, triglycerides or certain free fatty acids in Type 2 patients.

This same observation further suggests a method of inhibiting triglyceride formation. These methods, in general, comprise administering to a patient an effective amount of at least one xanthine-based compound. An effective amount is measured relative to the reduction or inhibition of triglycerides. This effect typically is on the order of at least about 10%, but more typically at least about 20%. More preferably, the effect should be at least about 30%.

An additional method contemplated entails increasing tissue glucose uptake. This method in general comprises contacting a tissue with an effective amount of at least one xanthine-based compound. This method may be performed in vivo or ex vivo, depending on the application. An effective amount is measured relative to the stimulation of glucose uptake, relative to a control. For example, it may be measured against the known effects of insulin. Thus an effective amount in this case would typically be on the order of at least about 10% of the effect of insulin, but more typically at least about 20%. More preferably, the effect should be at least about 30%.

The term "treating" in its various grammatical forms in relation to the present invention refers to preventing, curing, reversing, attenuating, alleviating, mining, suppressing or halting the deleterious effects of a disease state, disease progression, disease causative agent or other abnormal condition. Methods of prophylaxis are specifically encompassed by the term "treatment."

Although the foregoing detailed description and the following examples set forth representative preferred embodiments of the invention, they are not intended as exclusive embodiments. In view of the material presented, one of ordinary skill in the art readily would appreciate further embodiments that fall within the scope of the invention.

EXAMPLE 1

This example illustrates that lisofylline (LSF) treatment improved glucose tolerance and insulin action in female Zucker Diabetes Fatty (ZDF) rats and reduced blood glucose in sacrificed ZDF male rats. Sixteen ZDF male rats and eight ZDF female rats (approximately 8 weeks of age) were divided into two groups. Half were given LSF at 25 mg per kg of body weight via intraperitoneal injection twice a day. The rest of the animals were injected twice a day with vehicle solution only. Animals were weighed prior to each injection to precisely determine appropriate dose of agent. After seven days of treatment all rats underwent an oral glucose tolerance test (2 g glucose per kg of body weight) after which they remained on their respective treatment for another 48 hrs. Balon et al, *Am. J. Physiol.* 269: E745–52, 1995. Rats were then euthanized and blood and tissues were obtained. 2-deoxyglucose uptake in vitro in epitrochlearis muscle was performed as previously described. Balon et al., *J Appl. Physiol.* 77(6): 2519–22, 1994. Blood glucose was analyzed with a YSI glucose analyzer. Triglyceride and cholesterol were assayed as previously described. Balon et al, *Am. J. Physiol.* 269: E745–52, 1995. Animal body weight was not different in the two groups at the time of sacrifice (345±5 vs. 344±7 grams for males and 312±5 vs. 314±10 grams for females).

Fed state glucose values were measured 3 days after the treatment. The glucose concentration showed no difference after LSF treatment in male rats (267±24 mg/dl SEM for the LSF group vs. 262±18 for the vehicle group) or female rats (119±10 mg/dl for the LSF group vs. 105±12 for the vehicle group). The p value was 0.8773 for males and 0.3926 for females.

Oral glucose tolerance was monitored by analyzing the integrated area under the glucose tolerance curve at time points 0, 15, 30, 60 and 120 minutes. In the female rats, a statistical reduction in the area under the glucose tolerance curve (AUC) was observed with LSF treatment (24,095±1, 191 for the LSF group vs. 28,958±857 for the vehicle group, p<0.02) (FIG. 1). Furthermore, significant reduction in glucose concentration was also observed at the 15, 30, 45 and 60 minute time points in the rats treated with LSF. However, in the male rates, no significant difference in the AUC was observed after LSF treatment (27,301±2,405 for the LSF group vs. 26,932±1,536 for the vehicle group). Several male rats responded to LSF, but demonstrated with the large standard error of measurement (SEM). However, there was an indication that fasting glucose was reduced by LSF treatment (95±9 mg/dl for the LSF group vs. 106±4 for the vehicle group, p=0.1304).

Blood glucose and some other blood parameters were obtained at sacrifice. No difference in the blood cholesterol concentration was found in male or female rats treated with or without LSF.

| Cholesterol (mg/dl) | n | LSF | Vehicle |
|---|---|---|---|
| Males | 7 | 100 ± 3 | 100 ± 3 |
| Females | 4 | 78 ± 5 | 80 ± 7 |

However, LSF was found to reduce blood glucose level, triglyceride levels and the insulin concentration in the female rats.

| Glucose (mg/dl) | LSF | Vehicle | p |
|---|---|---|---|
| Males | 270 ± 27 | 270 ± 27 | 0.287 |
| Females | 103 ± 11 | 116 ± 6 | 0.36 |

The statistical insignificance (p=0.423) is due to a small n and variability. However, here was a tendency that triglyceride concentration was lowered by LSF treatment. Elevated riglycerides have been shown to be a risk factor for cardiovascular disease in Type 2 diabetes. In addition, elevated tissue triglycerides are associated with insulin resistance in skeletal muscle and reduced insulin secretion in pancreatic islets.

| Triglyceride (mg/dl) | n | LSF | Vehicle |
|---|---|---|---|
| Males | 7 | 630 ± 64 | 644 ± 58 |
| Females | 4 | 394 ± 118 | 540 ± 114 |

Sacrifice blood insulin values showed that insulin concentration (by RIA) was reduced by LSF treatment, especially in female ZDF rats. The insulin concentration ($\mu$U/ml) was reduced 32 percent in the females and 19.6 percent in the males. This is yet another indication that LSF is acting to increase glucose uptake, since insulin levels are typically elevated in this model (as in Type 2 patients) in order to compensate for high glucose levels by releasing more insulin. In other words, decreased insulin levels indicate improved insulin action in the presence of unchanged or reduced blood glucose levels.

| Insulin ($\mu$U/ml) | LSF | Vehicle | Reduction (%) |
|---|---|---|---|
| Males | 5.75 ± 1.1 | 7.07 ± 0.92 | 19.6 |
| Females | 7.27 ± 1.1 | 10.76 ± 2.0 | 32 |

In order to demonstrate that the xanthine-based compounds can act in combination with insulin, glucose uptake in epitrochlearis muscle was studied in isolated muscles from both male and female rats in response to insulin exposure (200 $\mu$U/ml). The study analyzed LSF effect on 2-deoxyglucose uptake in response to insulin exposure. Again, treatment with LSF did not show any difference in insulin response in the muscle of male rats. Consistently, however, in the presence of insulin, glucose uptake in female rats was improved with LSF treatment. Thus, the female rats were more insulin-resistant because their response to insulin involved lowered glucose uptake.

| Stimulation of 2-deoxyglucose Uptake by Insulin Exposure | n | LSF | Vehicle | p |
|---|---|---|---|---|
| Males | 8 | 0.79 ± 0.38 | 1.08 ± 0.38 | 0.6136 |
| Females | 4 | 1.51 ± 0.69 | −0.29 ± 0.84 | 0.1483 |

Because the female ZDF model is a glucose-intolerant, insulin resistant model that maintains insulin secretion, and LSF improved glucose uptake, both alone and in response to insulin in female ZDF rats, the xanthine-based compounds may act in two ways to promote tissue glucose uptake: (1) directly and (2) indirectly, by improving/restoring insulin activity. Accordingly, irrespective of mechanism, LSF may be used to reduce blood glucose either in the presence or absence of insulin.

EXAMPLE 2

This example illustrates the effect of LSF on glucose control in female ZDF rats maintained on a high fat diet, which has been reported to induce further insulin resistance and hyperglycemia in female ZDF model. In this study, the method was identical to that described in EXAMPLE 1 except that an in situ approach to measure insulin sensitivity was used. This method is called the Hindquarter perfusion technique. Balon et al, *Hypertension* 23(6) [part 2]: 1036–39, 1994. The study was carried out for 30 days to evaluate any prolonged effect by LSF.

Although there was variability in the baseline glucose values in this particular batch of ZDF female animals, the animals were matched prior to drug group assignment (117±0.17 mg/dl and 114±15 mg/dl). The glucose concentration showed a trend during the course of the study that it was lowered due to LSF treatment. On day 18 of treatment, morining glucose concentration was 208±18 mg/dl for the LSF group and 264±20 mg/dl for the vehicle group (p<0.06). The fasting blood glucose concentration was measured on the day of the glucose tolerance test. The glucose concentration was 109±9 mg/dl for the vehicle group vs. 98±7 mg/dl for the LSF group. While not statistically significant, the data showed a trend of reduced glucose concentration with LSF treatment.

Interestingly, LSF reduced significantly the level of hemoglobin A1C (a glycated hemoglobin) concentration from 10.5±0.5 percent to 8.8±0.48 percent in female ZDF rats (p<0.02). Such results indicate that the xanthine-based compounds reduce blood glucose over longer periods of time.

Confirmatory, hindquarter-perfusion results demonstrate that LSF affects significantly glucose in the presence of high insulin concentrations. Thus, at 31–33 days, the rats were prepared for hindquarter perfusion as described. Balon et al, *Hypertension* 23(6) [part 2]: 1036–39, 1994. The observed glucose uptake by perfused rat (weight-matched animals) hindquarter ($\mu$mol/g) is shown as following.

| Insulin (μU/ml) | Vehicle | LSF |
|---|---|---|
| 0 | 0.92 ± 0.27 | 0.99 ± 0.25 |
| 200 | 2.44 ± 0.21 | 2.82 ± 0.30 |
| 20,000 | 4.35 ± 0.24 | 5.88 ± 0.66* |

Values are ± SEM of 7–8 observations.
*denotes significance between groups at P = 0.0369.

In conclusion, LSF can improve insulin response in ZDF female rats fed a high fat diet (induces insulin resistance) after long-term (30 day) treatment with LSF. Interestingly, a quite significant reduction of hemoglobin A1C was found in LSF-treated animals, indicating that LSF-mediated blood glucose reduction is sustained in vivo.

EXAMPLE 3

This example confirms the effect of xanthine-based compounds on glucose tolerance as demonstrated in EXAMPLE 1, using a larger population of animals. The same protocol described in EXAMPLE 1 was adopted. First, the effects of LSF on glucose level and tolerance were measured. In this study, there were eleven rats for both LSF and vehicle groups. On the day of the glucose tolerance curve was obtained, the fasting glucose concentration was 99.5±5 mg/dl for the vehicle group and 97.5±4 for the LSF group (p=0.759). There was a trend of LSF-mediated glucose uptake in animals treated at 15, 30, and 120 minutes, and statistically significant LSF-mediated glucose uptake at 60 min (p<0.03). The glucose concentration (mg/dl) is summarized as following.

| Time (min) | Vehicle | LSF | p |
|---|---|---|---|
| 15 | 189 ± 7 | 175 ± 6 | 0.143 |
| 30 | 251 ± 11 | 230 ± 5 | 0.107 |
| 60 | 290 ± 12 | 252 ± 9 | <0.03 |
| 120 | 209 ± 13 | 175 ± 13 | 0.085 |

In addition, the integrated area under the glucose tolerance curve was significantly smaller in the LSF group (25,137±809) than that in the vehicle group (28,526±976) (p<0.02).

Again, hind-limb perfusion was done, with no significant effect, however. This is likely due to experimental differences. In this experiment, in contrast to EXAMPLE 2, the rats were fed a normal diet, had normal blood glucose, and were treated for 7 days instead of 30. Hence, it is likely that longer treatments are needed.

| Insulin (μU/ml) | Vehicle | LSF |
|---|---|---|
| 0 | 0.53 ± 0.21 | 0.76 ± 0.34 |
| 200 | 1.92 ± 0.25 | 1.75 ± 0.10 |
| 20,000 | 4.35 ± 0.24 | 4.27 ± 0.22 |

Values are ± SEM of 7–8 observations.

EXAMPLE 4

This example further substantiates the ability of xanthine-based compounds to alleviate insulin resistance in an animal model, and suggests that they do so by altering fatty acid metabolism. ZDF rats were used and experiments were conducted as above.

Female ZDF rats, maintained on a normal chow diet, were given LSF at 25 mg/kg body weight (BW) intraperitoneally, twice a day for 7–10 days. Results showed a singificant improvement in oral glucose tolerance, with a reduction of are under under the glucose curve:

Experiment 1: 25,137±809 mg %×120 min. for LSF versus 28,526±997 for vehicle; P<0.02.

Experiment 2: 12,045±1258 mg %×120 min. for LSF versus 17,936±1672 for vehicle; P<0.02.

When LSF was administered at the same dose for 31 days, levels of hemoglobin A1C were significantly reduced in animals on a high fat (48%) diet: 8.8±0.4% for LSF versus 10.5±0.5% for vehicle; P<0.03.

LSF also improved insulin-stimulated glucose uptake in hindquarter perfusion experiments: 5.88±0.66 μmol/g/h for LSF versus 4.35±0.24 for vehicle; P <0.04.

Isolated epitrochlearis muscle from animals treated with the same dose of LSF for 10 days showed increased insulin-stimulated 2-deoxyglucose transport: 5.9±0.63 μmol/g/min for LSF versus 10.5±0.05% for vehicle; P<0.01.

In order to ascertain a possible mechanism for the above observations, levels of 9-bydroxyoctadecadienoic acid (9-HODE) and linoleic acid (LA) were measured. 9-HODE is a key oxidative product of LA that may be involved in peripheral insulin resistance. Animals were treated as above.

Plasma LA levels were measured by electron-capture gas chromatography essentially. Levels were markedly increase in obese animals: 12.7±1.0 μg in obese versus 3.7±0.4 in lean; P<0.001.

Plasma levels of 9-HODE were measured by reverse phase high performance liquid chromatography (HPLC), LSF treatment reduced levels only in obese Zucker rats: 15.5±4 ng/ml for LSF versus 45.8±12 for vehicle; P<0.05. (Non-obese data not shown.)

The foregoing data indicate an association of increased 9-HODE with insulin resistance. They further show that both insulin resistance and oxidized fatty acid levels are decreased with LSF treatment, suggesting that the ameliorative action of LSF is mediated by modulating fatty acid metabolism.

EXAMPLE 5

This example demonstrates that xanthine-based compounds reverse glucose-induced down-regulation of tyrosine kinase activation of the human insulin receptor beta subunit, at least in part, by by-passing the insulin receptor, initiating the signaling cascade down-stream of that receptor. The results also indicate that xanthine-based compounds can enhance the ability of insulin to induce tyrosine autophosphorylation of the insulin receptor, which is one of the key early signaling events in insulin-mediated actions.

These methods used below are drawn from Li et al, Biochemistry 31: 12455–62 (1992). This experiment utilized Chinese hamster ovary fibroblasts that have been engineered to stably overexpress the human insulin receptor (CHO-HIR) ) as a cell model for insulin resistance induced by the presence of glucose. CHO-HIR cells ($3 \times 10^6$ cells /data point) were cultured in elevated (40 mM) or normal (8 mM) glucose for 7 to 14 days under otherwise standard conditions.

Cells were serum-depleted and samples were treated with 200 μM LSF for 30 hours. Samples were harvested, washed with phosphate-buffered saline and lysed in 0.5 ml of lysis buffer. Lysis buffer contains 50 mM Tris-HCl, pH 7.4; 1 μg/ml leupeptin; 1 μg/ml pepstatin; 1 μg/ml aprotinin, 10 mM N-alpha-benzoyl-L-arginyl-ethyl ester and 0.1 mM phenylmethylsulfonyl fluoride. After forty minutes, samples were clarified by centrifugation at 12 000×g for 15 minutes. Aliquots of the supernatant fractions, containing the insulin receptor, were treated with 100 nM insulin for 2 hr at 4° in the presence of gamma $^{32}$P-labeled ATP at 25° C. for 40 min. Protein (10 μg per lane) was resolved by SDS polyacrylamide gel electrophoresis. Phosphorylated insulin receptor was detected by autoradiography.

Results are depicted in FIG. 2. The arrow indicates the position of the insulin receptor beta subunit. It can be seen that in the presence of 8 mM glucose, insulin stimulates phosphorylation of the beta subunit (compare lanes 2 and 1). This stimulation is inhibited by 40 mM glucose (compare lanes 6 and 2). LSF stimulates the phosphorylation of the beta subunit in 8 mM glucose in the absence of insulin (lane 3) and enhances insulin- induced phoshorylation (compare lanes 4 and 3). LSF also reverses the inhibition of beta subunit phosphorylation by 40 mM glucose both in the presence of insulin (compare lanes 8 and 6) and in the absence of insulin (compare lanes 7 and 5), with greater stimulation being seen in the presence of insulin.

Lanes 6 and 2 show insulin-treated samples that were cultured in 40 mM (high) glucose or 8 mM (normal) glucose, respectively. A comparison of lanes 6 and 2 shows that high glucose levels decrease the amount of insulin-induced insulin receptor phosphorylation. Lane 3 demonstrates that LSF alone, without insulin treatment, stimulates phosphorylation of the insulin receptor. Lane 8 shows that LSF restored the ability of insulin to induce phosphorylation of the insulin receptor in insulin resistant cells. Lane 7 shows that LSF alone induces receptor phosphorylation in cells treated with high glucose.

We claim:

1. A method of treating a patient with Type II diabetes, impaired glucose tolerance, obesity, dyslipidemia, hyperuricemia, impaired fibrinolysis, or polycystic ovary disease, comprising administering to a patient that suffers from Type II diabetes, impaired glucose tolerance, obesity, dyslipidemia, hyperuricemia, impaired fibrinolysis, or polycystic ovary disease an effective amount of at least one xanthine-based compound, or a pharmaceutically acceptable salt thereof, having the following structure:

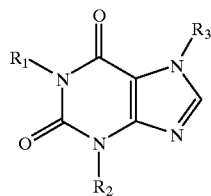

wherein:
R$_1$ is an R enantiomer of an ω-1 secondary alcohol-substituted alkyl (C$_{5-8}$), wherein said alcohol moiety is optionally esterified;
R$_2$ is alkyl (C$_{1-12}$), optionally containing one or two nonadjacent oxygen atoms in place of a carbon atom; and
R3 is CH3 or H.

2. A method according to claim 1, wherein said compound is lisofylline.

3. A method according to claim 1, wherein said effective amount is sufficient to reduce elevated blood glucose level of the said patient.

4. A method according to claim 3, wherein said effective amount is sufficient to reduce elevated blood glucose level of the said patient by at least about 10%.

5. A method according to claim 1, wherein said effective amount is sufficient to increase sensitivity of the patient to insulin.

6. A method according to claim 5, wherein said effective amount increases insulin sensitivity by at least about 10%.

7. A method according to claim 1, wherein said patient suffers from Type 2 diabetes.

8. A method of treating Type 2 diabetes-associated lipid disorders, comprising administering to a patient an effective amount of at least one xanthine-based compound or a pharmaceutically acceptable salt thereof, having the following structure:

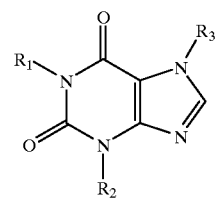

wherein:
R$_1$ is an R enantiomer of an ω-1 secondary alcohol-substituted alkyl (C$_{5-8}$), wherein said alcohol moiety is optionally esterified;
R$_2$ is alkyl (C$_{1-12}$), optionally containing one or two nonadjacent oxygen atoms in place of a carbon atom; and
R$_3$ is CH$_3$ or H.

9. A method according to claim 8, wherein said compound is lisofylline.

10. A method of inhibiting triglyceride formation, comprising administering to a patient an effective amount of at least one xanthine-based compound or a pharmaceutically acceptable salt thereof, having the following structure:

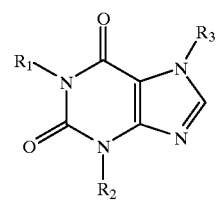

wherein:
R$_1$ is an R enantiomer of an ω-1 secondary alcohol-substituted alkyl (C$_{5-8}$), wherein said alcohol moiety is optionally esterified;
R$_2$ is alkyl (C$_{1-12}$), optionally containing one or two nonadjacent oxygen atoms in place of a carbon atom; and
R$_3$ is CH$_3$ or H.

11. A method according to claim 10, wherein said compound is lisofylline.

12. A method according to claim 1, wherein said patient suffers from impaired glucose tolerance or Type II diabetes.

* * * * *